(12) United States Patent
Koller

(10) Patent No.: US 9,079,024 B2
(45) Date of Patent: Jul. 14, 2015

(54) PROTECTIVE BODY FOR INSERTION INTO BODY CAVITY

(71) Applicants: Christian Lechner, Rothis (AT); Franz Karl Bohler, Feldkirch (AT); Gunar Koller, Feldkirch (AT)

(72) Inventor: Gunar Koller, Feldkirch (AT)

(73) Assignees: Gunar Koller, Feldkirch (AT); Christian Lechner, Röthis (AT); Franz Karl Böhler, Feldkirch (AT)

(*) Notice: Subject to any disclaimer, the term of this patent is extended or adjusted under 35 U.S.C. 154(b) by 0 days.

(21) Appl. No.: 14/386,928

(22) PCT Filed: Dec. 21, 2012

(86) PCT No.: PCT/AT2012/000320
§ 371 (c)(1),
(2) Date: Sep. 22, 2014

(87) PCT Pub. No.: WO2013/138825
PCT Pub. Date: Sep. 26, 2013

(65) Prior Publication Data
US 2015/0041685 A1    Feb. 12, 2015

(30) Foreign Application Priority Data
Mar. 22, 2012 (AT) .................. A 354/2012

(51) Int. Cl.
*A61N 5/10* (2006.01)
*G21F 3/00* (2006.01)
*A61B 19/00* (2006.01)

(52) U.S. Cl.
CPC .. *A61N 5/10* (2013.01); *G21F 3/00* (2013.01); *A61B 2019/4045* (2013.01); *A61B 2019/5466* (2013.01); *A61N 5/1014* (2013.01);
(Continued)

(58) Field of Classification Search
USPC ............................................ 250/515.1, 519.1
See application file for complete search history.

(56) References Cited

U.S. PATENT DOCUMENTS 3,872,856 A    3/1975  Clayton
5,190,990 A *  3/1993  Eichmiller .................... 523/137
(Continued)

FOREIGN PATENT DOCUMENTS

DE    3512318       12/1985
WO    9959501       11/1999
WO    2011026662    3/2011

OTHER PUBLICATIONS

Kaanders, Johannes H. A. M., et al. "Devices in Valuable Head and Neck Radiotherapy", Radiation Oncology Biol. Phys. vol. 23, pp. 639-645, The University of Texas M.D. Anderson Cancer Center, Houston, TX, Jan. 3, 1992.

(Continued)

*Primary Examiner* — Kiet T Nguyen
(74) *Attorney, Agent, or Firm* — Volpe and Koenig, P.C.

(57) ABSTRACT

A protective body for insertion into a body cavity of a human or animal body for the protection of tissue and/or organs that are not to be irradiated when carrying out radiation therapy, wherein the protective body (1) includes at least one absorber body (2) designed to absorb radiation and having at least one curved surface (3) that delimits the absorber body, and the absorber body (2) has a density at 20° C. of at least 5 gram per cubic centimeter, preferably of at least 10 gram per cubic centimeter.

18 Claims, 13 Drawing Sheets

(52) U.S. Cl.
CPC ............ *A61N 5/1015* (2013.01); *A61N 5/1016* (2013.01); *A61N 5/1071* (2013.01); *A61N 2005/1018* (2013.01); *A61N 2005/1094* (2013.01)

(56) References Cited

U.S. PATENT DOCUMENTS

| | | | |
|---|---|---|---|
| 5,550,383 | A | 8/1996 | Haskell |
| 7,053,013 | B1 * | 5/2006 | Nosov et al. .................. 442/180 |
| 2006/0224034 | A1 | 10/2006 | Reever |
| 2006/0244034 | A1 | 11/2006 | Sakurai et al. |
| 2012/0167897 | A1 | 7/2012 | Bettega |

OTHER PUBLICATIONS

Ang, K. Kian et al. "Radiotherapy for Head and Neck Cancers", Indications and Techniques, Fourth Edition, Wolters Kluwer Health, 2006.

* cited by examiner

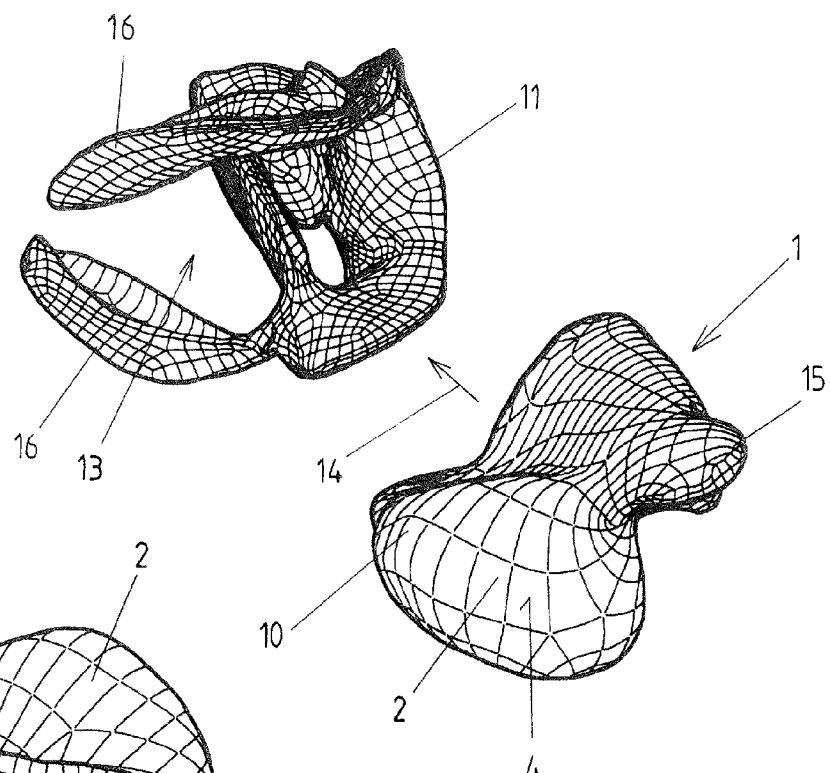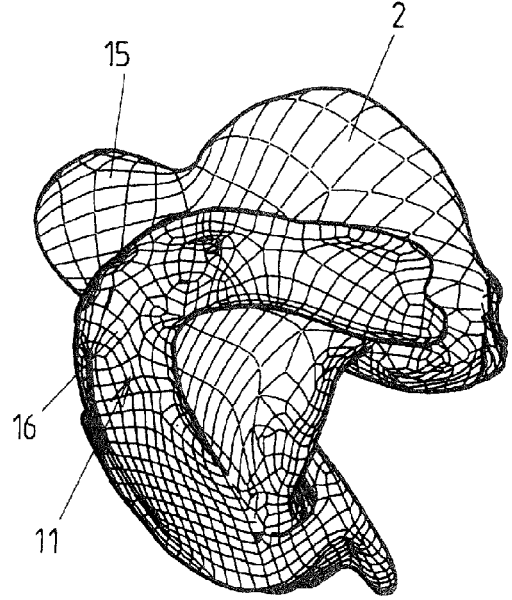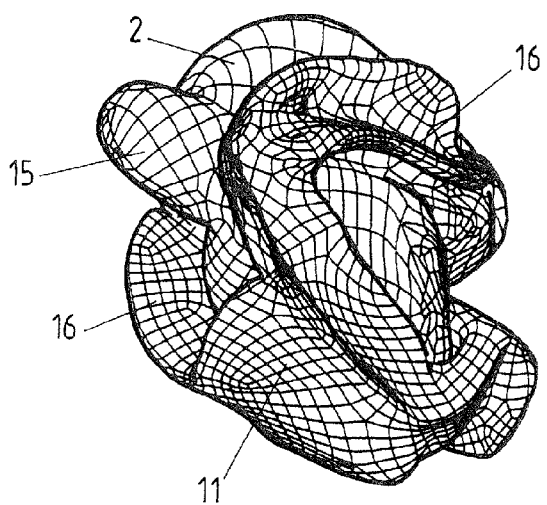

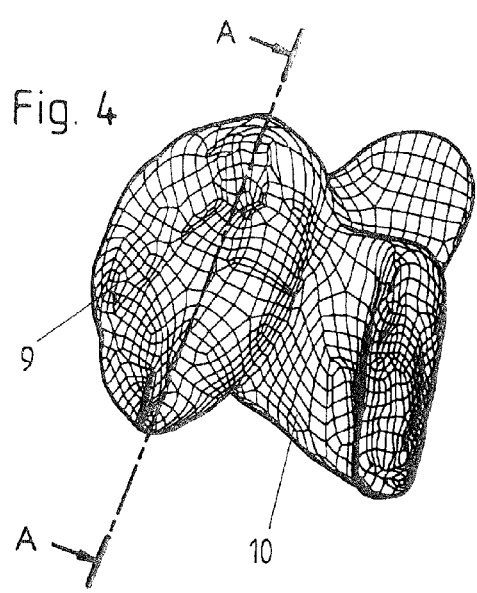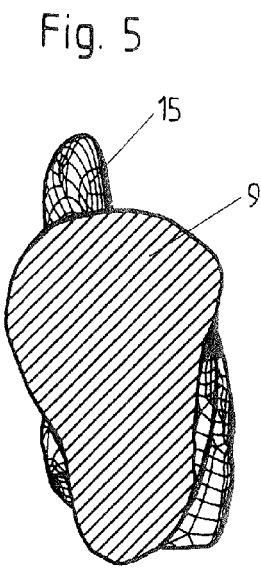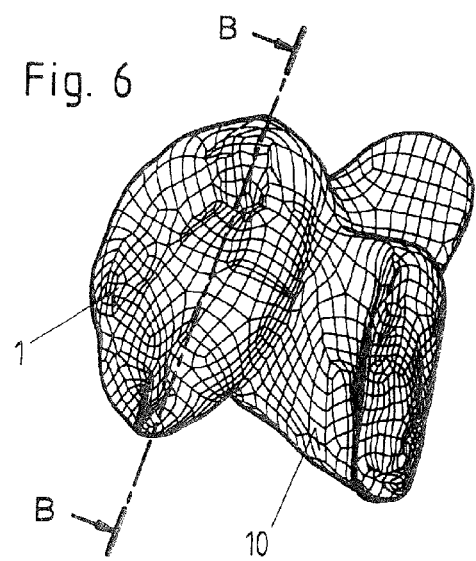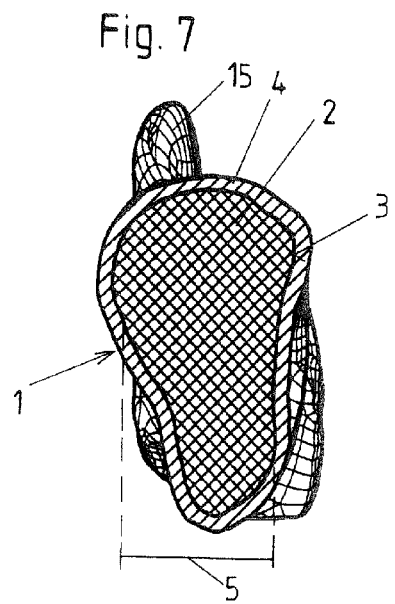

Fig. 28
Fig. 29
Fig. 30
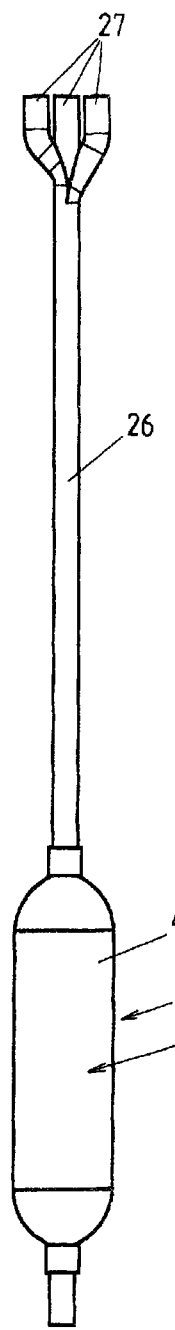
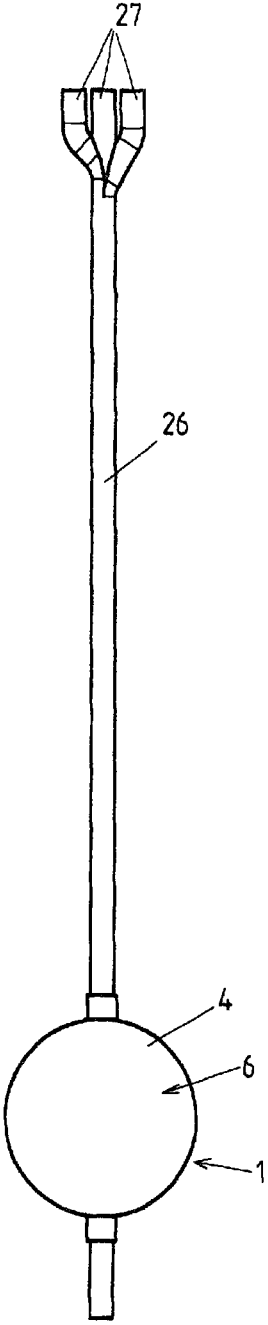
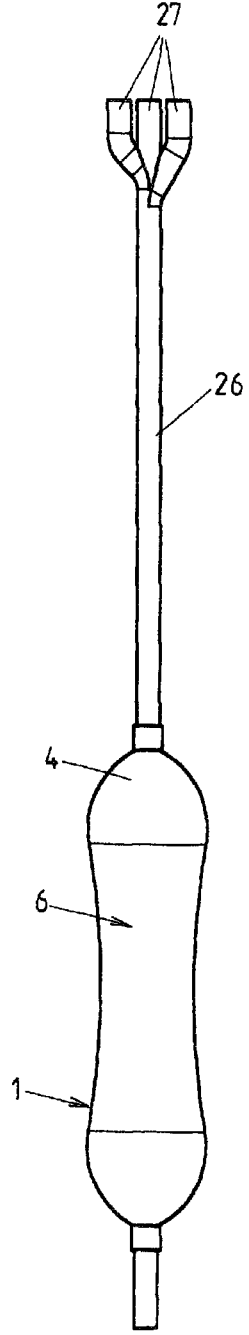

PROTECTIVE BODY FOR INSERTION INTO BODY CAVITY

BACKGROUND

The present invention relates to a protective body for insertion into a body cavity of a human or animal body for the protection of tissue and/or organs that are not to be irradiated when carrying out radiation therapy.

In medicine nowadays, radiation therapy is used in many forms in the treatment of patients with cancer and tumors. This involves applying a sufficiently high radiation dose to the area to be irradiated, in particular the tumor, while seeking to ensure that the healthy tissue areas and organs, in particular adjacent to the tumor, are damaged as little as possible, if at all, by the radiation.

A tissue protector for use in the oral cavity is known from WO 2011/026662 A1. It basically involves a plastic component which, by being shaped individually to the patient, serves to move the tongue, lips and other tissue parts out of the beam path, such that these get the smallest possible dose of radiation and, as a result, there is the least possible chance of damage to otherwise healthy tissue. Moreover, WO 2011/026662 A1 also discloses that lead plates, which are advantageously exchangeable, that can additionally be applied, if appropriate, to the tissue protector disclosed there.

SUMMARY

The object of the present invention is to provide an alternative possibility for the design of protective bodies of the abovementioned type.

To this end, the invention provides that the protective body comprises at least one absorber body designed to absorb radiation and having at least one curved surface that delimits the absorber body, and the absorber body has a density at 20° C. of at least 5 grams per cubic centimeter, preferably of at least 10 grams per cubic centimeter.

In the invention, and in the physical realization thereof in the form of corresponding protective bodies, another approach is thus chosen to the question of how tissues and organs that are not to be irradiated can be protected from irradiation during radiation therapy. The approach proposed here no longer involves these tissue parts that are to be protected being moved out of the way, but instead entails corresponding body cavities being filled by means of the absorber body at the places required for this radiation protection, such that this absorber body absorbs the radiation in the area in which the tissue and/or organs not to be irradiated are intended to be protected. To be able to afford this protective function, the absorber bodies must have at least one curved surface that delimits them, since there are practically no straight surfaces existing in the human or animal body. Furthermore, the absorber body must have a density of at least 5 grams per cubic centimeter, preferably of at least 10 grams per cubic centimeter. This density is thus to be determined at 20° C. under normal conditions.

Protective bodies according to the invention cannot only be used in the oral cavity, as is known from WO 2011/026662 A1, but also in other natural body cavities, e.g. the nasal cavity, the vagina, the anus and large intestine. However, it is equally possible for artificial body cavities to be created surgically and for corresponding protective bodies to be inserted into them to ensure that, during radiation therapy, tissue and/or organs that are not to be irradiated are protected from too high a dose of radiation. Through the use of protective bodies according to the invention, it is also possible to obtain new beam paths in radiation therapy. For the best possible adaptation to the shape of the respective body cavity and/or of the tissue and/or organ to be protected, the absorber body, or the surface delimiting the latter, is curved anatomically.

Protective bodies according to the invention can be used both in teletherapy and also in brachytherapy. While the radiation can thus act on the patient's body from the outside, it is just as possible to use protective bodies according to the invention when the radiation source or the radiation sources are arranged in and/or directly on the body. In teletherapy, that is to say in irradiation from the outside, a relatively new development called IMRT (intensity-modulated radiation therapy) is available in which irradiation is provided from a multiplicity of sources or fields, e.g. 70-80. Protective bodies according to the invention are particularly suitable for this use too. In addition, protective bodies according to the invention can also be used in high LET irradiation and in other high-energy irradiation techniques.

In preferred embodiments of the invention, the protective body has a cover which encloses the absorber body, preferably completely, and which is made from a different material than the absorber body, preferably from at least one plastic or from aluminum or an aluminum alloy, or at least has such a different material.

In the case of toxic absorber materials of the absorber body, the cover can serve in particular to protect the body from a negative effect of the toxic absorber material. However, the cover can also serve, additionally or alternatively, to prevent or minimize backscatter electrons occurring on the absorber body during the irradiation. The cover is preferably made from a non-toxic, biocompatible and expediently radiation-transparent material. A large number of plastics are suitable for this purpose. Examples that may be mentioned are acrylics, methacrylate and many other polymers and also monomers. Covers made from aluminum or aluminum alloy are also conceivable. The covers should as far as possible enclose the absorber body completely, or at least to the extent that no toxic effect can emanate from the absorber body. Particularly suitable materials for the cover are at any rate those which, in the case of an absorber body made from lead, and in an elution test (especially according to EN ISO 11885) in which the eluate of the test specimen over 24 hours by the overhead shaking method with an eluent of 3% acetic acid and a weight ratio between eluent and test specimen of 5:1, yield a maximum of 200 μg of lead in the eluate after 24 hours. The cover preferably has, preferably all over, a wall thickness of at least 1 millimeter, preferably of at least 2 millimeters. The absorption effect of different absorber bodies is dependent on the nature of the irradiation and on the nature of the absorber material. However, in order to obtain a suitably high absorption, it is generally expedient if the absorber body has, at least in some areas, a minimum diameter of 4 millimeters, preferably of 10 millimeters. If in doubt, this minimum diameter is to be measured in the direction of the beam path.

In contrast to WO 2011/026662 A1, in which a viewing window is necessarily provided, the protective body, in the assembled state, expediently has no such opening for visual monitoring of an operating area. With suitable planning and arrangement, this is also not needed. On the contrary, the protective body can therefore be used not only postoperatively or preoperatively but also in primary radiation therapy or primary radiation chemotherapy without operation.

The absorber body expediently includes a metal, preferably lead or mercury. It can also be comprised entirely thereof. In many embodiments, the protective bodies and absorber bodies form inherently rigid, solid bodies. In another type of embodiment, however, it is also possible that the cover encloses at least one fillable volume of the protective body, wherein a liquid absorber material, preferably mercury, is introduced or can be introduced into the volume in order to form the absorber body. In these embodiments, the cover encloses a hollow space and therefore a fillable volume of the protective body into which a liquid absorber material can be introduced in order to form the absorber body. Kinds of catheter systems can thus be created which can be brought to the suitable location in the patient's body through relatively small openings. It is only when these catheter-like protective bodies have reached their end position that the fillable volume in the cover is filled by introduction of the corresponding absorber material and thereby obtains its contour, which is preferably determined by the shape of the cover and which is provided for the irradiation procedure. Before the removal of the catheter-like protective body, the absorber material can be withdrawn again from the hollow space or volume, such that the removal of the protective body from the human or animal body can also take place through a relatively small opening in the body.

In a further refinement of the invention, at least the absorber body has an opening and closing arrangement in order to open and close an opening that extends through the absorber body, preferably through the protective body. These variants make it possible for the opening in the absorber body to be left open, by means of the opening and closing arrangement, in certain irradiation procedures and to be closed in other ones. The opening and closing arrangements can in particular be systems of leaves and slides. They are preferably opening and closing arrangements that can be electrically actuated and, if appropriate, remotely controlled. Hydraulic or pneumatic actuation is also possible via suitable admission and discharge lines.

Besides the protective body itself, the invention also relates to a kit with at least one protective body according to the invention, wherein the kit comprises, in addition to the protective body, at least one replacement body made from a different material, preferably a more radiation transparent material, wherein the protective body and the replacement body have an identical outer contour to each other at least in some areas, preferably all over. For example, the replacement body can be made from the same material as the cover, i.e. preferably from plastic, aluminum or an aluminum alloy. The replacement body is expediently made, at least for the most part, from a considerably more radiation transparent material. The radiation transparency can be adapted, as in the case of the cover, to the radiation transparency of the tissue of the human or animal body. The replacement bodies can then be used in particular for computed tomography tests, which are needed for planning the radiation therapy. By means of the identical contour, and by inserting the replacement bodies into the corresponding body cavity, it is possible, in the computed tomogram used for planning, to exactly simulate the spatial relationships arising with the protective body, such that exact planning of the radiation therapy is possible. In other words, the kit that has been described permits very exact planning and performance of radiation therapy. In particular, erroneous interpretation of artifacts is avoided. Thus, in the course of planning, a possible approach or possible method is to introduce the replacement body into an artificial or natural body cavity and then, using an imaging method, for example CT, MRT and the like, to image the geometric relationships in the body with the aid of the replacement body.

Even with the protective body designed as a hollow body, exact planning is possible by realization of a corresponding kit. Provision is preferably made that the protective body has a cover which encloses the absorber body, preferably completely, and which is made from a different material than the absorber body, preferably from at least one plastic or from aluminum or an aluminum alloy, or at least has such a different material, wherein the cover encloses at least one volume of the protective body, wherein a liquid absorber material, preferably mercury, is introduced or can be introduced into the volume in order to form the absorber body, and a fluid that is more radiation transparent than the liquid absorber material, preferably air or water or saline solution, is introduced or can be introduced in order to form the replacement body. Of course, other suitable and more radiation transparent fluids can also be used. By introduction of the more radiation transparent fluid into the fillable volume predetermined by the shape of the cover, it is also ensured here that the protective body and the replacement body have an identical outer contour to each other at least in some areas, preferably all over. The cover is designed such that the same outer contour is obtained both by filling with absorber material and also by filling with the more radiation transparent fluid.

In a further refinement of the invention, a kit with at least one protective body is provided with at least one opening and closing arrangement, wherein the kit comprises, in addition to the protective body, at least one replacement body made from a different material, preferably more radiation transparent material, wherein the replacement body and the opened and/or closed protective body have an identical outer contour to each other at least in some areas, preferably all over. For example, provision can be made that the replacement body has an opening and closing arrangement identical to the protective body and made from a more radiation transparent material.

Moreover, kits are preferably provided which additionally have at least one support body which can be inserted at least partially into the body cavity and on which and/or in which the protective body and optionally the replacement body can be arranged, preferably can be fixed, in a defined position relative to the support body. The support body can then be used to ensure that the replacement body and optionally also the protective body can be brought exactly to the desired end position. It is expedient here if the protective body and optionally also the replacement body are held in the end position on the support body with a detachable form fit, e.g. by means of a snap-in engagement. If the body cavity in question is one that is accessible from the outside, it is particularly expedient that the protective body and the replacement body can be removed from the support body from the outside and can be reinserted into it.

For exact positioning during irradiation, provision is made, in preferred embodiments, that the support body has at least one fixing device for fixing the support body in the body or outside the body. The fixing of such a support body in the body of the person or animal to be treated can be effected, for example, by suitable fastening to a bone. Many different options are conceivable for this purpose, e.g. screwing on, adhesive bonding, or other fastening possibilities by means of bands, tensioning straps or the like. A type of fixing outside the body is also possible. This can be achieved, for example, in the manner shown in FIGS. 9 and 10 of WO 2011/026662 A1. Alternatively, such fixing devices can also be provided directly on the protective body in all of the embodiments mentioned.

Markings, e.g. made of radiation opaque material, can be mounted both on the protective body itself and also on the support body and/or on the replacement body for position determination during the planning and/or radiation therapy, in order to obtain visible orientation points in the computed tomogram.

In order to monitor the radiation dose during the irradiation, radiation-measuring means or devices, e.g. dosimeter films, detectors and the like, can be arranged on the protective body, on the support body and/or on the replacement body, so as to be able to determine the corresponding radiation dose at certain locations.

In this context, radiation-measuring means designate indicator bodies which, due to their chemical and/or physical change, permit a corresponding indication of the radiation dose that occurs. A radiation-measuring device designates suitable sensors or detectors, i.e. an appliance that permits a preferably running measurement of the radiation dose.

In the context of the invention, it is possible for suitable protective bodies, support bodies and/or replacement bodies to be produced in a manner individually matched to the particular requirements during the radiation therapy of the respective patient. By suitable measurements of the areas of the body to be treated, e.g. by means of computed tomography, it is possible for partially or fully automated production of the protective bodies to take place. From the known absorber material, the known radiation paths, the geometries of the areas to be shielded and the provided radiation doses, it is possible for the shape, size and choice of material in the absorber material to be determined in an automated or partially automated manner.

BRIEF DESCRIPTION OF THE SEVERAL VIEWS OF THE DRAWINGS

Further features and details of various embodiments of the invention are explained in the following description of the figures on the basis of various alternatives according to the invention. In the figures:

FIGS. 1 to 7 show a first embodiment according to the invention;

FIGS. 28 to 30 show three further embodiments according to the invention;

DETAILED DESCRIPTION OF THE PREFERRED EMBODIMENTS

Figure 8:
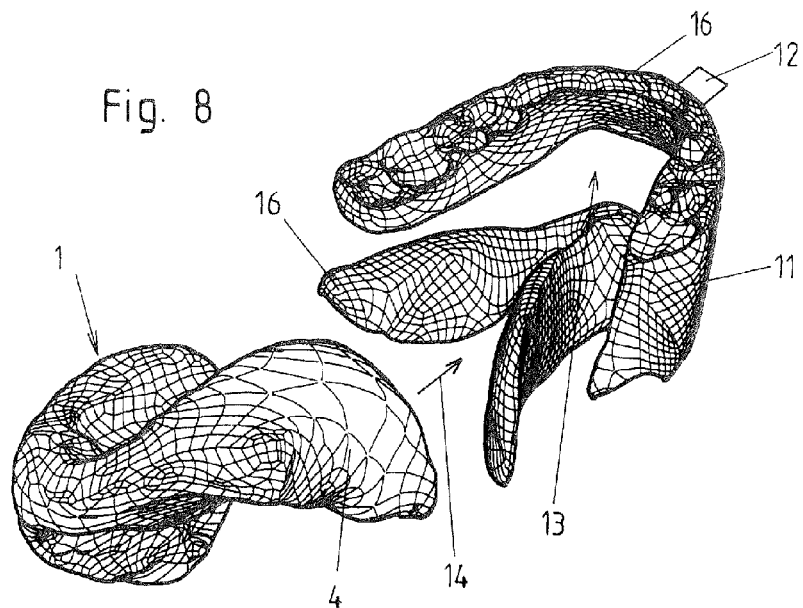
FIGS. 8 to 14 show a second embodiment according to the invention.

The first illustrative embodiment as per FIGS. 1 to 7 comprises a kit with a protective body 1 according to the invention, a matching support body 11 and a replacement body 9, which has an identical outer contour 10 to the protective body 1. This first illustrative embodiment of the invention is intended to be placed in the oral cavity of the patient. The support body 11, which is preferably made of a similarly radiation transparent material like the human body, e.g. of a suitable plastic, has two tooth parts 16. When the patient for whom this illustrative embodiment was produced bites with his upper and lower jaws and teeth onto the tooth parts 16, the support body 11 is positioned exactly and in a defined manner in the oral cavity. An exact positioning in the support body 11 is achieved for the protective body 1 when the latter is pushed in insertion direction 14 as far as the end position in the receiving opening 13 provided for it. In the end position, the protective body 1 is held and positioned with a form fit and with its position defined. In the first illustrative embodiment, the insertion direction 14 and the receiving opening 13 are designed such that the protective body 1 can be pushed in and removed through the mouth with the support body 11 simultaneously fitted. The support body 11 can thus remain in the patient's mouth when changing between replacement body 9 and protective body 1. In order to be able to obtain a good grip on the protective body 1, the latter has, like the replacement body 9, a grip part 15. FIGS. 2 and 3 illustrate the protective body 1 in its inserted end position in the support body 11. An exact positioning is obtained as a result of the form fit in this end position. FIG. 6 shows the protective body 1 of this first illustrative embodiment from another perspective. The section line BB is also indicated there. The cross section assigned to this section line BB is shown in FIG. 7. The latter clearly shows how the absorber body 2, e.g. made of lead, is completely enclosed by the cover 4. The surface 3 of the absorber body 2 is curved anatomically such that the protective body, i.e. the absorber body 2 along with the cover 4, fills the body cavity, in this case the oral cavity, to the required extent. As regards the choice of material and thickness of the cover 4, see what was stated at the outset. Moreover, for suitable radiation absorption, the aforementioned minimum diameter 5, shown here by way of example, should also be observed at the appropriate locations.

FIG. 4 shows the replacement body 9 which, when carrying out the planning computed tomogram, can be inserted into the support body 11 in an identical way to the protective body 1. The outer contour 10 of the replacement body 9 is for this purpose made identical to the outer contour 10 of the protective body 1. FIG. 5 shows the cross section AA according to FIG. 4. As regards the choice of material of the replacement body 9, see what was stated at the outset. For example, it is thus possible for this replacement body 9 to be produced from the same material, in particular from the same plastic, as that of the support body 11 or of the cover 4.

The second illustrative embodiment, as per FIGS. 8 to 14, is also intended to be placed in the oral cavity of the patient. Here, however, the protective body 1 and therefore also the replacement body 9 are pushed onto the support body 11 from behind. This means that, in this illustrative embodiment, the support body 11 has to be removed from the patient's mouth when changing between protective body 1 and replacement body 9. For the purpose of exact positioning, this illustrative embodiment shows, on the support body 11, the fixing device 12 that can be used to fix it, as is shown for example in FIGS. 9 and 10 of WO 2011/026662 A1.

Figure 9:
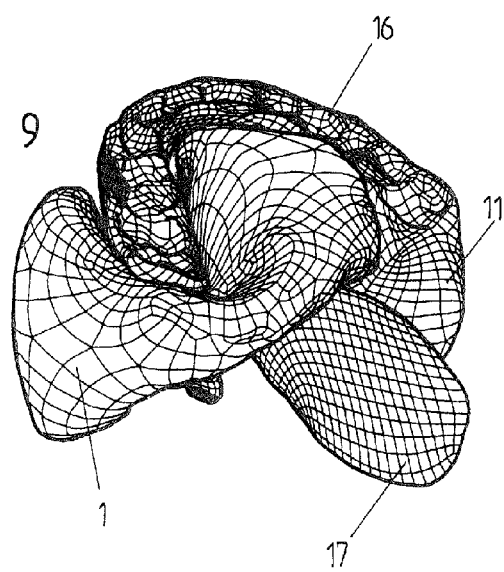
Figure 10:
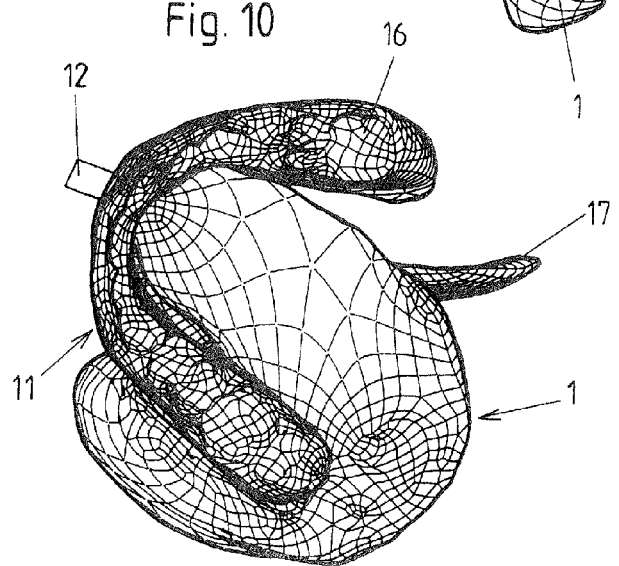
Figure 11:
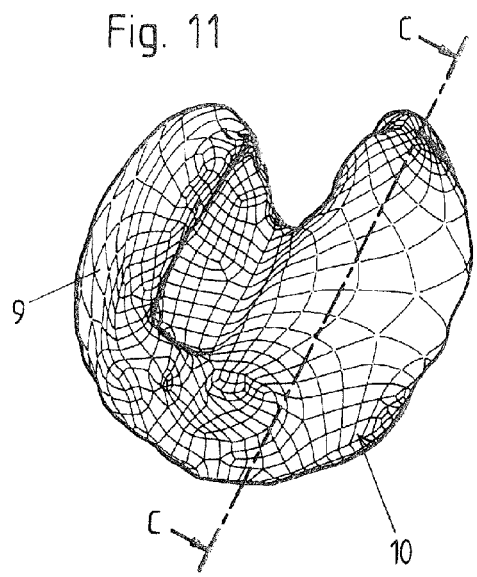
Figure 12:
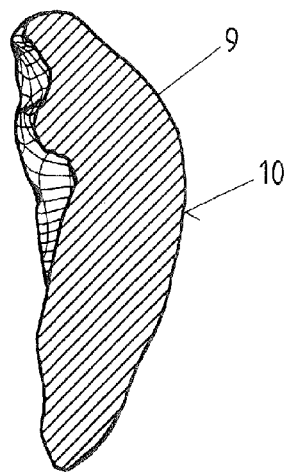
Figure 13:
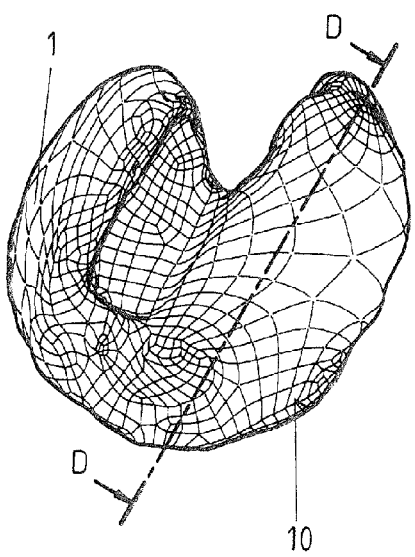
Figure 14:
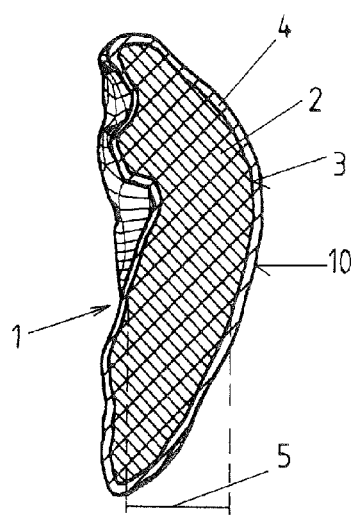

In the second illustrative embodiment, a snap-fit connection, here in the form of a snap-fit lever 17, is provided for securing the protective body and the replacement body in the respective end position in the support body 11. When the end position is reached, both the protective body 1 and also the replacement body 9 snap into place. The snap-fit lever 17 then has to be actuated to release them. FIG. 8 shows the support body 11 and the protective body 1 separate from each other, and the insertion direction 14 in which the protective body 1 is pushed into the corresponding receiving opening 13 of the support body 11. FIGS. 9 and 10 illustrate the interconnected state from two different viewing directions. FIG. 11 in turn shows the replacement body 9. FIG. 12 shows the cross section through this replacement body 9 along the section line CC from FIG. 11. FIG. 13 shows the protective body 1 and the section line DD. The cross section assigned to the section line DD is shown in FIG. 14. As regards the cover 4 and the design of the absorber body 2, what was stated in respect of the first illustrative embodiment applies once again.

Figure 15:
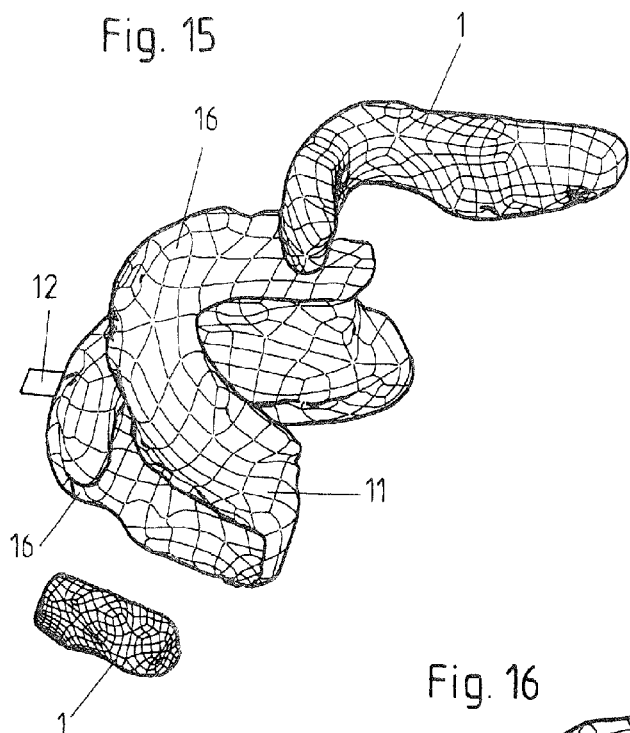
FIGS. 15 to 19 show a third embodiment according to the invention.
Figure 16:
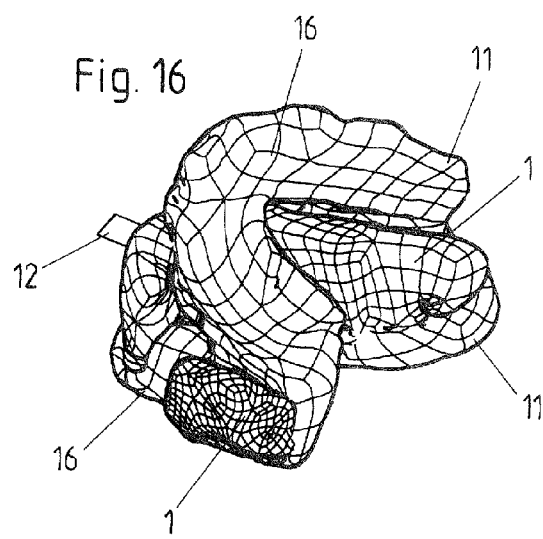
Figure 17:
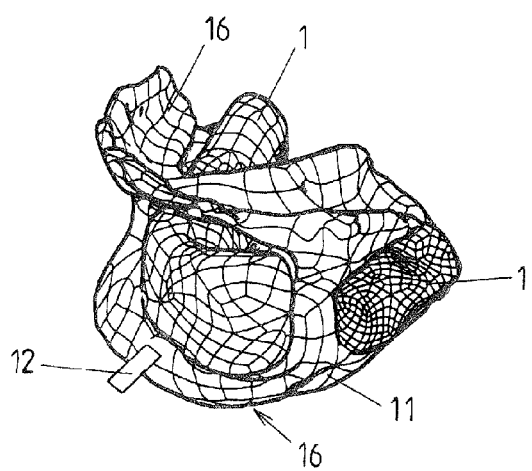
Figure 18:
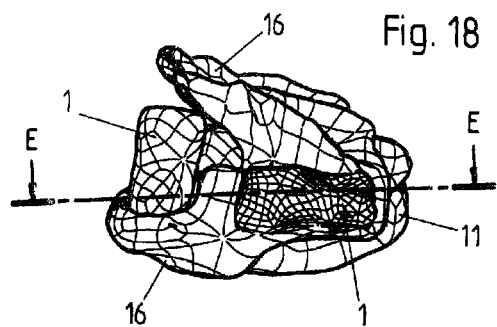

FIGS. 15 to 19 show a further illustrative embodiment of a support body 11, here however with two protective bodies 1 according to the invention. Here once again, the support body 11 is intended to be placed together with the protective bodies 1 into the patient's mouth. The replacement bodies 9 possibly required for the planning computed tomogram are not shown here. However, they can be provided as in the previously explained illustrative embodiments and can each have the same outer contour 10 as the respective protective body 1 that they are intended to replace in the planning computed tomogram. In this illustrative embodiment, the fixing device 12 is likewise arranged on the support body 11. It serves the same purpose as in the already described second illustrative embodiment. The protective bodies 1 likewise in each case have an internal absorber body 2, which is covered completely by a suitable cover 4. FIG. 15 shows an exploded view in which the two protective bodies 1 are detached from the support body 11. FIGS. 16 to 18 show different views in which the protective bodies 1 are held with a form fit in their end position in the support body 11.

Figure 19:
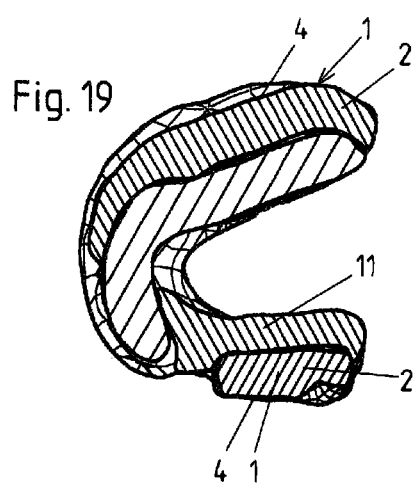

FIG. 19 shows a horizontal section along the section line EE from FIG. 18. This illustrative embodiment basically shows that it is possible to use not just one protective body 1 but also a plurality of protective bodies 1, if this is necessary for protecting the healthy tissue and/or organ areas during a defined radiation therapy.

Figure 20:
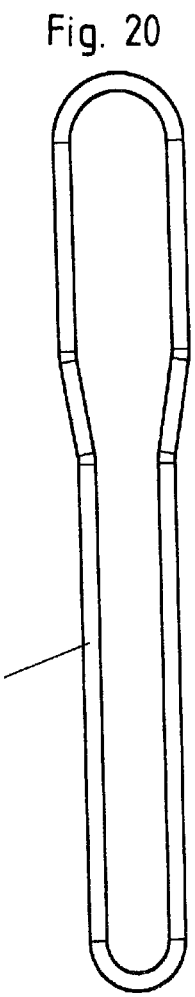
FIG. 20 shows an auxiliary spoon.

FIG. 20 shows an auxiliary spoon 18 which, in configurations of the invention according to the first three illustrative embodiments, is used to lift the lips of the patient over the support body 11. It will be noted that edges can be formed on the support body 11 and/or protective body 1 and/or replacement body 9 so as to be able to better fix the lips of the patient in their intended position. This of course applies to a wide variety of types of use in the mouth area.

Figure 21:
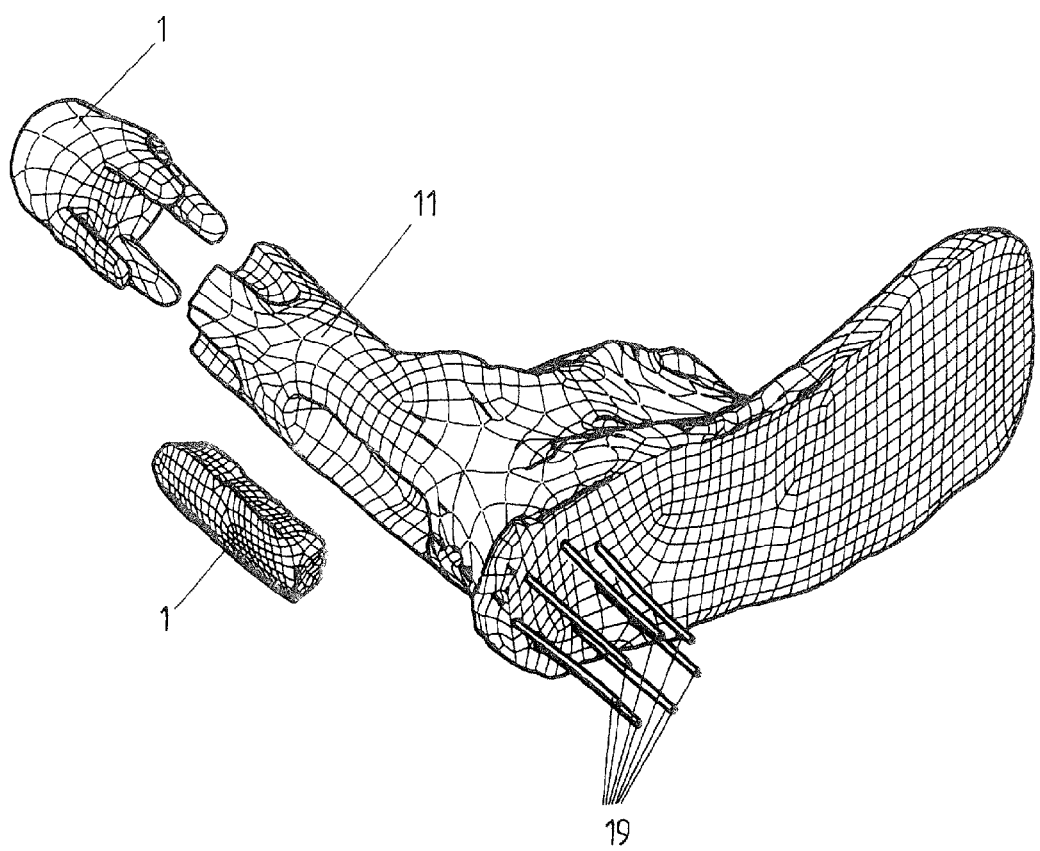
FIGS. 21 to 23 show a fourth embodiment according to the invention.
Figure 22:
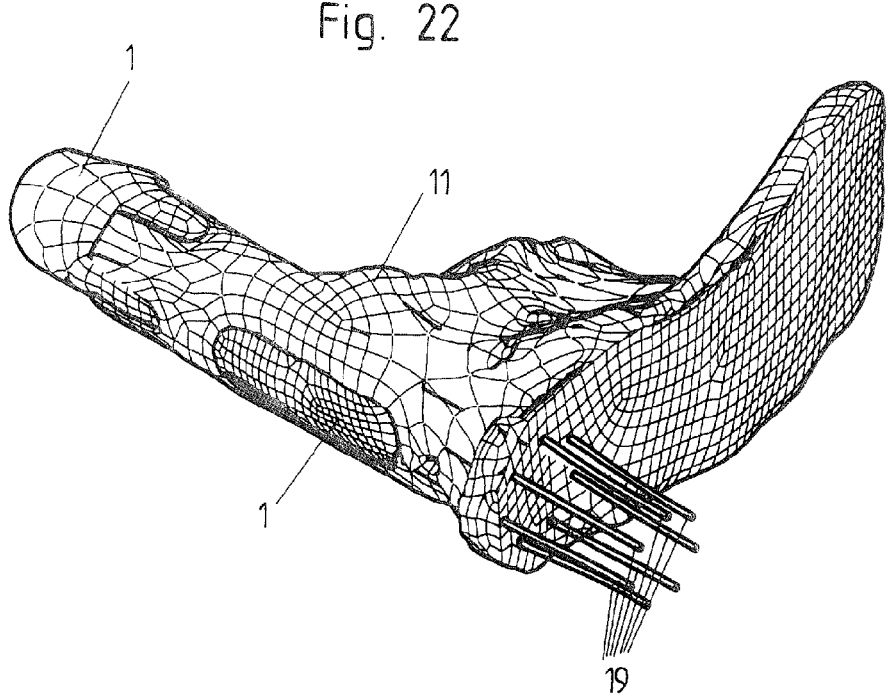
Figure 23:
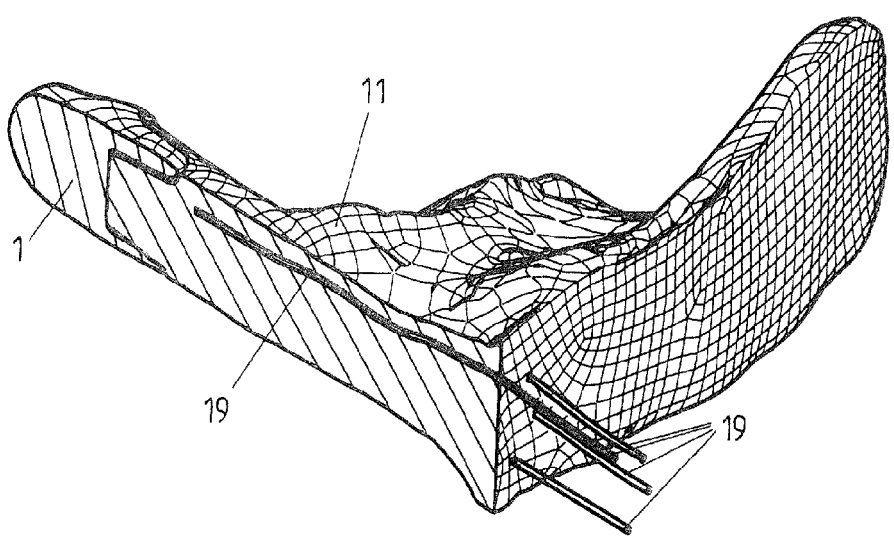

FIGS. 21 to 23 show a further illustrative embodiment of the invention with a support body 11 having two protective bodies 1. The illustrative embodiment shown here is intended to be inserted into a patient's vagina. The protective bodies 1 once again each have an inner absorber body 2 (although this is no longer shown explicitly here), each of which is completely enclosed by a cover 4. As in the other illustrative embodiments too, the absorber body 2 can once again be lead or another suitable absorber material. The support body 11 can again be produced from a suitable plastic or other suitable material, in particular from the same material as the cover 4. What was generally stated above also applies here.

Also in this fourth illustrative embodiment according to the invention, the protective bodies 1 are held with a form fit in the support body 11. If so required for a planning computed tomogram, they can also be replaced by replacement bodies 9 that are suitably provided with the same outer contour 10. This embodiment variant shows by way of example that, in order to carry out brachytherapy, provision can be made that at least one radiation source is arranged directly in the support body 11. The channels 19 are provided for this purpose in the illustrative embodiment shown, with suitable radiation sources being able to be inserted or pushed into said channels. As an alternative to the radiation sources, however, radiation detectors can of course also be arranged in these channels 19 or generally in the support body 11, in order to measure the radiation dose at a defined location. These ideas are set out for explanatory purposes in this illustrative embodiment. However, they can equally well be provided in all the other illustrative embodiments with support bodies 11.

The four above-described illustrative embodiments of the invention are all intended to be inserted into natural body cavities. In the text below, examples of variants of the invention are explained which are intended to be inserted possibly surgically, especially surgically, into an artificially accessible or artificially created body cavity of the human or animal body.

Figure 24:
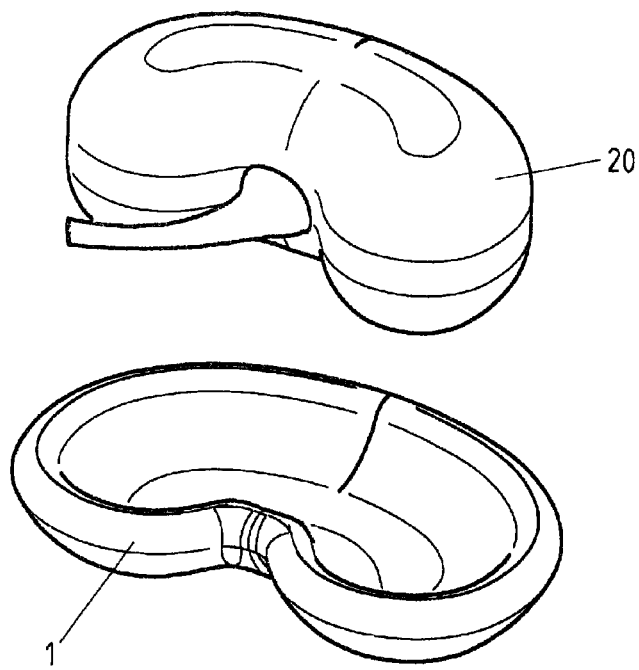
FIGS. 24 and 25 show a fifth embodiment according to the invention.
Figure 25:
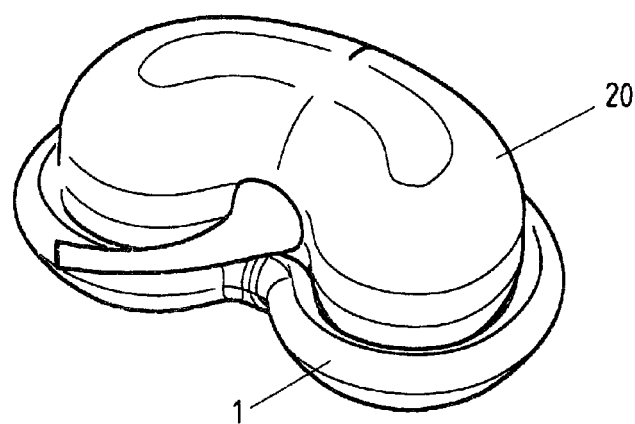

In the illustrative embodiment according to FIGS. 24 and 25, the protective body 1 is designed like a bowl, its shape adapted to the kidney 20. As is shown in FIG. 25, this bowl-shaped protective body 1 is placed with one side onto the kidney 20, such that the latter is suitably protected from unnecessary radiation. This protective body 1 is also comprised of an inner absorber body 2, made of suitable absorber material, and of a cover 4, although this is not explicitly shown here.

It will be noted for completeness that, also in applications of this kind on artificially created or artificially opened body cavities, a support body 11 can be provided, which can then be fixed for example on a bone or on another body part in order to hold the protective body 1 in a defined end position. If appropriate, replacement bodies 9 can also be suitably used here together with the support body 11 for a planning computed tomogram.

Figure 26:
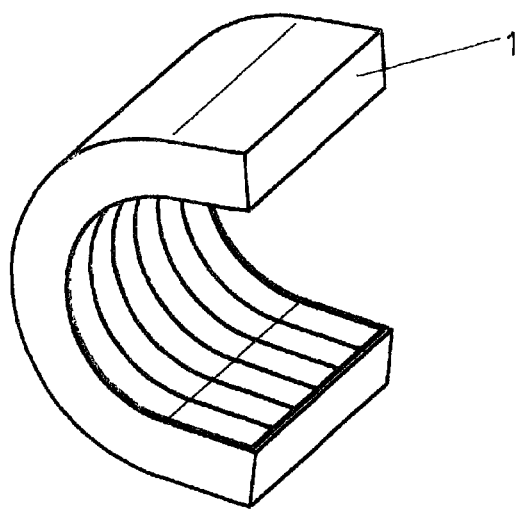
FIGS. 26 and 27 show a sixth embodiment according to the invention.
Figure 27:
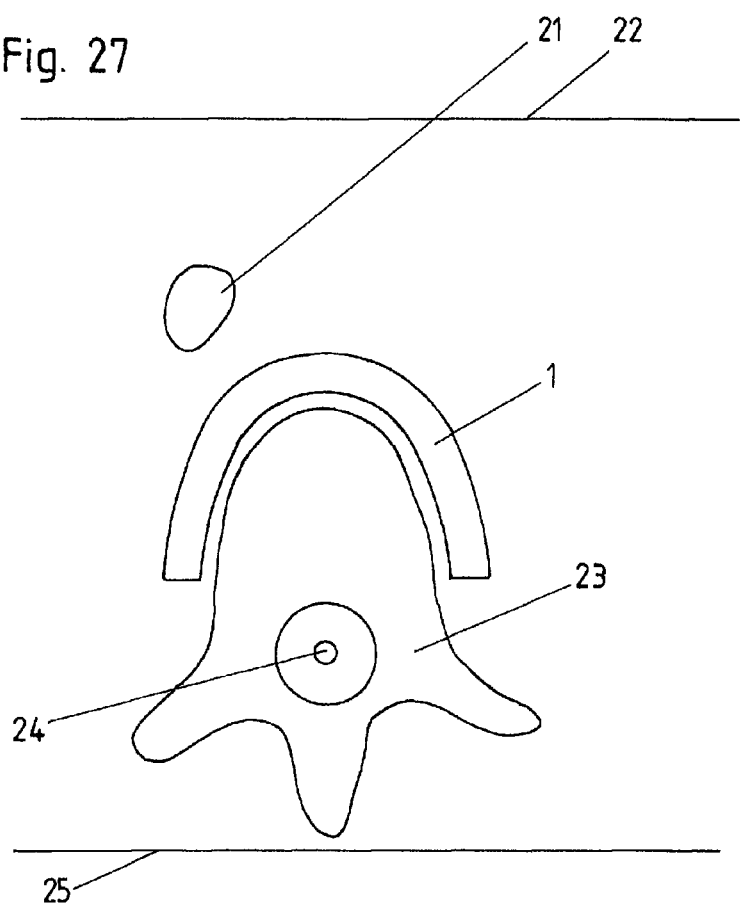
Figure 31:
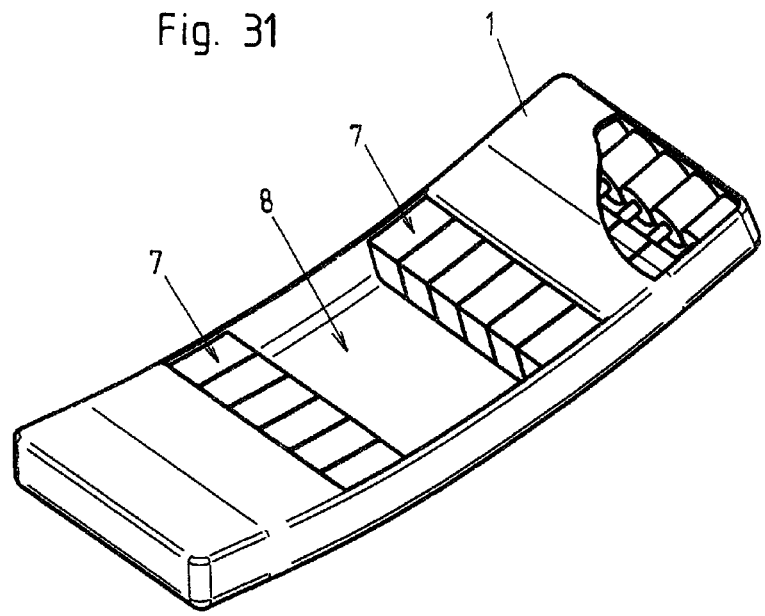
FIGS. 31 and 32 show two further embodiments.

FIGS. 26 and 27 show a further illustrative embodiment which is intended to be inserted into an artificial body cavity, i.e. a body cavity created by surgical intervention. This entails a protective body 1 of U-shaped cross section which, for example, can be used to protect the spinal column. This protective body 1 is also preferably once again comprised of at least one absorber body 2 with a suitable cover 4, even though this is not explicitly shown here. FIG. 27 is a very schematic representation of the protective body 1 from FIG. 26 introduced surgically into the body of the patient. It shows the schematically indicated tumor 21 which is to be treated by means of radiation therapy, and which lies between the abdominal wall 22 and the vertebra 23. When performing teletherapy from the direction of the abdominal wall 22, it is necessary for the vertebra 23, lying behind the tumor 21, and in particular for the spinal cord 24 to be protected from irradiation. For this purpose, the protective body 1, adapted in terms of its shape to the shape of the vertebral body of the vertebra 23, is placed in the form shown around the vertebral body. In this way, when the tumor 21 is irradiated from the direction of the abdomen, the vertebra 23 and in particular the spinal cord 24 are suitably protected. The patient's back is designated schematically by reference number 25.

FIGS. 28 to 30 are schematic views of illustrative embodiments of the invention in which the cover 4 encloses at least one fillable volume 6 of the protective body 1, and a liquid absorber material, preferably mercury, is or can be introduced into the volume 6 in order to form the absorber body 2. In the illustrative embodiments shown here, the filling takes place via the respective attachment nozzles 27 and the inlet and outlet tubes 26. To insert the protective body 1 formed in this way, this kind of catheter can be brought to the suitable location in the human or animal body by way of a body opening that is as small as possible. Only then is the liquid absorber material 2, e.g. mercury, introduced through the attachment nozzle 27 and the inlet and outlet tube 26 into the fillable volume 6 in the cover 4. The radiation therapy can be performed when the volume 6 is suitably filled with absorber material. To remove the catheter, it is advisable first to extract the absorber material again from the fillable volume 6 through the inlet and outlet tubes 26 and the attachment nozzles 27, before the catheter is removed through the suitably small opening in the body. The cover 4 preferably entails flexible balloon-shaped or hose-shaped bodies which are able to expand when filled with absorber material and are able to contract when absorber material is removed. Of course, in certain suitable configurations and fields of use, covers 4 are also conceivable which form a rigid or at least in some areas rigid and/or partially rigid hollow wall.

Figure 32:
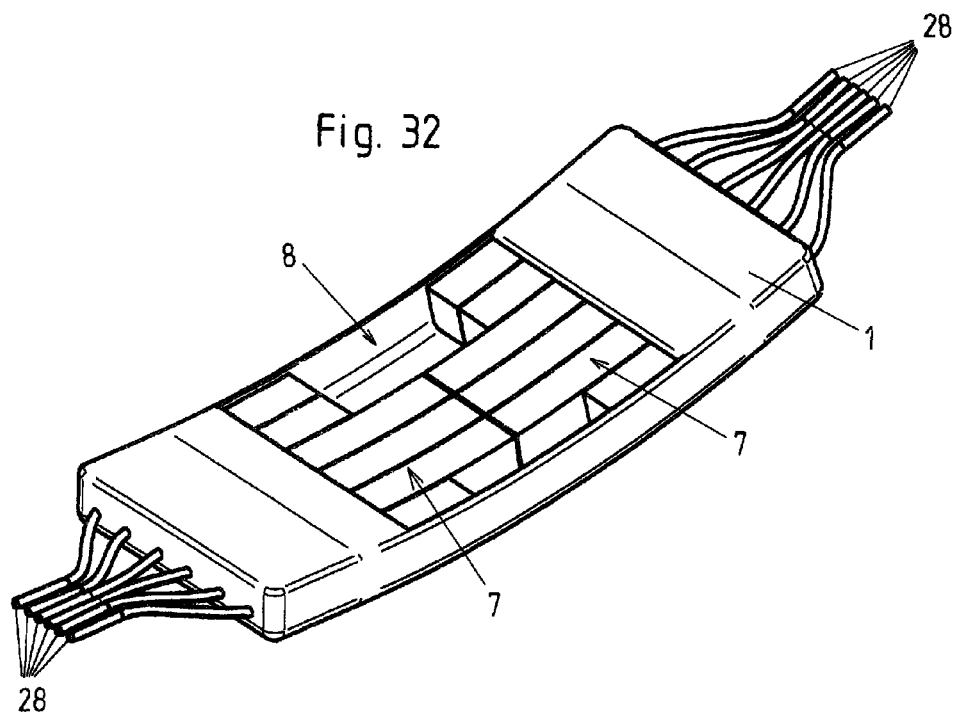
Figure 33:
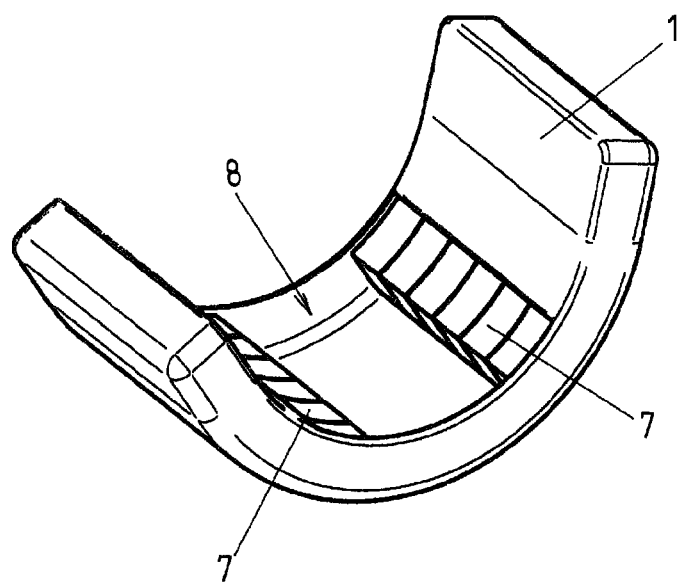
FIGS. 33 and 34 show a further illustrative embodiment according to the invention.
Figure 34:
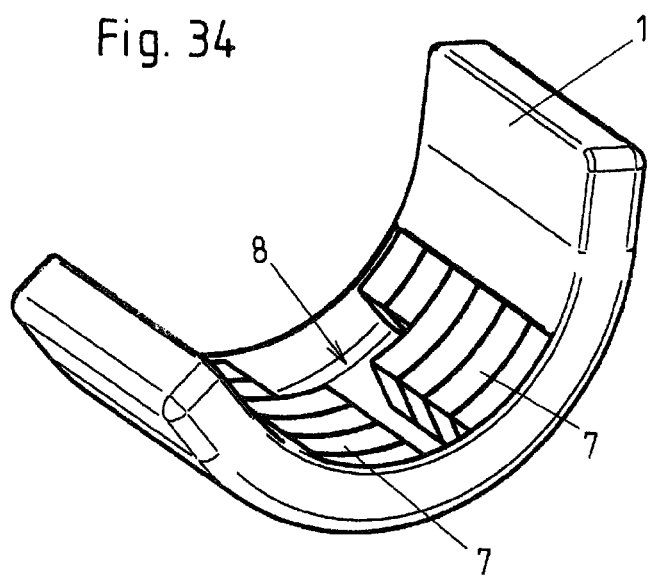

The two final illustrative embodiments as per FIGS. 31 to 34 show variants of protective bodies 1 according to the invention in which at least the absorber body 2, here in each case the entire protective body 1, has an opening and closing arrangement 7 in order to open and close a continuous opening 8 that extends through the absorber body 2, in this case through the entire protective body 1. These variants of the invention can in particular be used when the protective body 1 has to be inserted surgically into an artificial cavity in the human or animal body and radiation therapy then has to be carried out in which certain beam paths are to be permitted in some radiation forms and are intended to be closed in other directions of irradiation. Here too, although not explicitly shown, the protective bodies 1 are again each comprised of an inner absorber body 2, which is provided with a suitable cover 4. The opening and closing arrangement 7 is in the form of a system of slides which, preferably under remote control from outside the body to be treated, can be moved between their closed position and their open position. In the illustrative embodiments shown, provision is even made that each slide of the opening and closing arrangement 7 can be controlled individually. The actuation can be effected electrically via corresponding motors and batteries and a corresponding receiver in the protective body 1 and via a remote control system. FIG. 32 shows an alternative variant in which the slides of the opening and closing arrangement 7 are controlled hydraulically or pneumatically via the tubes 28.

KEY TO THE REFERENCE NUMBERS 1 protective body
2 absorber body
3 surface
4 cover
5 minimum diameter
6 fillable volume
7 opening and closing arrangement
8 opening
9 replacement body
10 outer contour
11 support body
12 fixing device
13 receiving opening
14 insertion direction
15 grip part
16 tooth part
17 snap-fit lever
18 auxiliary spoon
19 insertion channel
20 kidney
21 tumor
22 abdominal wall
23 vertebra
24 spinal cord
25 back
26 inlet and outlet tube
27 attachment nozzle
28 tube

The invention claimed is:

1. A kit comprising: at least one protective body for insertion into a body cavity of a human or animal body for protection of tissue or organs that are not to be irradiated when carrying out radiation therapy, comprising, at least one absorber body designed to absorb radiation and having at least one curved surface that delimits the absorber body, and the absorber body has a density at 20° C. of at least 5 grams per cubic centimeter; at least one replacement body made from a different material, wherein the protective body and the replacement body have an identical outer contour to each other at least in some areas; and at least one support body which is insertable at least partially into the body cavity and on which or in which the protective body and the replacement body can be arranged in a defined position relative to the support body.

2. The kit as claimed in claim 1, further comprising a cover which at least partially encloses the absorber body and which is made from or comprises a different material than the absorber body.

3. The kit as claimed in claim 2, wherein the cover has a wall thickness of at least 1 millimeter.

4. The kit as claimed in claim 2, wherein the cover encloses at least one fillable volume of the protective body, and further comprising a liquid absorber material introduced into the volume in order to form the absorber body.

5. The kit as claimed in claim 4, wherein the liquid absorber material is mercury.

6. The kit as claimed in claim 2, wherein the cover completely encloses the absorber body.

7. The kit as claimed in claim 2, wherein the cover comprises at least one plastic, aluminum, or an aluminum alloy.

8. The kit as claimed in claim 1, wherein the absorber body has, at least in some areas, a minimum diameter of 4 millimeters.

9. The kit as claimed in claim 1, wherein at least the absorber body has an opening and closing arrangement in order to open and close an opening extending through the absorber body.

10. The kit as claimed in claim 9, wherein the opening and closing arrangement comprises a system of leaves or slides.

11. The kit as claimed in claim 1, wherein the absorber body comprises metal.

12. The kit as claimed in claim 1, further comprising a radiation-measuring device.

13. The kit as claimed in claim 12, wherein the radiation measuring device comprises at least one of dosimeter films or radiation detectors.

14. The kit as claimed in claim 1, wherein the support body has at least one fixing device for fixing the support body in the body or outside the body.

15. The kit as claimed in claim 1, wherein the protective body has a cover which encloses the absorber body, and which is comprised of a different material than the absorber body, wherein the cover encloses at least one fillable volume of the protective body, and further comprises a liquid absorber material is introduced into the volume in order to form the absorber body, and a fluid that is more radiation transparent than the liquid absorber material is introduced in order to form the replacement body.

16. The kit as claimed in claim 1, wherein at least one of the protective body, the replacement body, or the support body has radiation-measuring device.

17. The kit as claimed in claim 1, at least one radiation source is arranged directly in the support body.

18. The kit as claimed in claim 1, wherein the absorber body has a density at 20° C. of at least 10 grams per cubic centimeter.

* * * * *